United States Patent [19]

Lugosi et al.

[11] 4,323,469

[45] Apr. 6, 1982

[54] PROCESS FOR O-ACYLATING PHENOL DERIVATIVES AND ACYLATING COMPOSITIONS FOR THIS PURPOSE

[75] Inventors: György Lugosi, Felsögöd; Antal S. May, Budapest; János Bodnár, Budapest; István Turcsán, Budapest; István Jelinek, Budapest; Éva Somfai, Budapest; Lászlo Simandi, Budapest, all of Hungary

[73] Assignee: Chinoin Gyógyszer és Vegyészeti Termékek Gyára R.T., Budapest, Hungary

[21] Appl. No.: 201,508

[22] Filed: Oct. 28, 1980

[51] Int. Cl.³ .............................................. C09K 3/00
[52] U.S. Cl. .......................... 252/182; 260/340.9 R; 260/346.22; 548/211; 560/32; 560/132
[58] Field of Search .................... 260/340.9 R, 346.22, 260/340.5 R; 560/32, 132; 548/211; 252/182

[56] References Cited

U.S. PATENT DOCUMENTS

| | | | |
|---|---|---|---|
| 2,623,050 | 12/1952 | Graenacher et al. | 252/182 |
| 2,945,877 | 7/1960 | Zima et al. | 560/32 |
| 3,531,425 | 9/1970 | Burk, Jr. et al. | 560/132 |
| 3,655,645 | 4/1972 | Jacques | 252/182 |
| 4,086,246 | 4/1978 | Toth et al. | 560/132 |
| 4,195,023 | 3/1980 | Mulvey et al. | 260/544 S X |

FOREIGN PATENT DOCUMENTS 1083803  6/1960  Fed. Rep. of Germany ........ 560/32

OTHER PUBLICATIONS

Chem. Abstracts 56:4748d.

*Primary Examiner*—Ethel G. Love
*Attorney, Agent, or Firm*—Karl F. Ross

[57] ABSTRACT

The invention relates to a process for the preparation of carbamic acid phenyl esters of the formula (I)

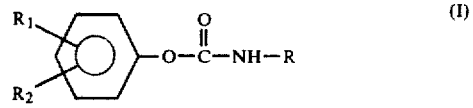

by acylating phenol derivatives of the formula (II)

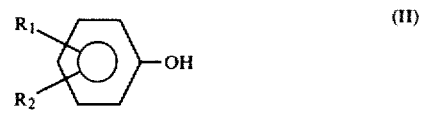

wherein
R is alkyl having 1 to 8 carbon atoms, aryl, cycloalkyl having 5 or 6 carbon atoms, aralkyl having 7 to 16 carbon atoms which groups can be substituted by one or more alkyl groups,
$R^1$ is hydrogen, alkyl having 1 to 4 carbon atoms, alkoxy having 1 to 4 carbon atoms or acylamino,
$R^2$ is hydrogen, halogen, alkyl having 1 to 4 carbon atoms or alkoxy having 1 to 4 carbon atoms, or if $R^1$ and $R^2$ represent alkyl and/or alkoxy, they can form together a carbocyclic ring.

According to the invention the phenol derivatives of the general formula (II), wherein $R^1$ and $R^2$ are as defined above, are reacted with N-carbamoyl-saccharin derivatives of the formula (IV)

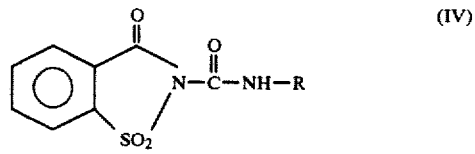

wherein R has the same meaning as defined above, in the presence of a base.

3 Claims, No Drawings

PROCESS FOR O-ACYLATING PHENOL DERIVATIVES AND ACYLATING COMPOSITIONS FOR THIS PURPOSE

The invention relates to a new process for O-acylating phenol derivatives and to acylating compositions suitable for this purpose. More particularly, the invention concerns a new process for the preparation of substituted carbamic acid phenyl ester derivatives of the formula (I)

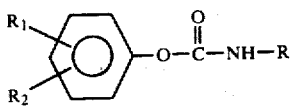

by O-acylating phenols of the formula (II)

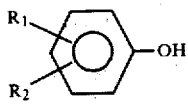

In the above formulae and throughout the specification

R is alkyl having 1 to 8 carbon atoms, aryl, cycloalkyl having 5 or 6 carbon atoms, aralkyl having 7 to 16 carbon atoms, which groups can be substituted by one or more alkyl groups, $R^1$ is hydrogen, alkyl having 1 to 4 carbon atoms, alkoxy having 1 to 4 carbon atoms or acylamino, $R^2$ is hydrogen, halogen, alkyl having 1 to 4 carbon atoms or alkoxy having 1 to 4 carbon atoms, or if $R^1$ and $R^2$ represent alkyl and/or alkoxy, they can form together a carbocyclic ring.

Compounds of the formula (I) are generally used for protecting plants from plant diseases.

A well-known process for the preparation of compounds of the formula (I), wherein $R^1$, $R^2$ and R are as hereinabove defined, consists in the addition of phenol derivatives of the formula (II) to isocyanates of the formula (III)

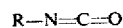

Due to the toxicity and mucous membrane irritating properties of the isocyanates, this process can, however, be carried out only under very strict labor-safety regulations, and is therefore rather cumbersome. A further disadvantage derives from the strongly exothermic character of the isocyanate addition reaction, which involves further technological problems, especially when isocyanates with a low boiling point are used, and may also lead to undesired side reactions. Moreover, certain isocyanates can be stored and transported only under special conditions, which involves further expenses and their accessability is restricted.

An alternative possibility for the preparation of compounds of the formula (I) consists in the reaction of compounds of the formula (II) with monosubstituted carbamic acid chlorides. The monosubstituted carbamic acid chlorides are, however, instable compounds (unlike their disubstituted analogs) and are easily transformed into isocyanates while hydrochloric acid is split off. These unstable compounds can be prepared also by the addition reaction of isocyanate and hydrochloric acid. It can, however, not be expected that a nucleophilic agent (for example a compound of the formula (II)) can be acylated without splitting off hydrochloric acid. Moreover, the disadvantages listed in the preceding paragraph are to be faced increasingly when carrying out this process.

Compounds of the formula (I) can also be prepared by reacting compounds of the formula (II) with phosgene and acylating an amine of the formula $R-NH_2$ by the chloroformic acid ester derivative obtained. This process, however, due to the extreme toxicity of phosgene gas, is highly disadvantageous.

It has now been found that carbamic acid phenyl ester derivatives of the formula (I) can be prepared with an excellent yield, in high purity by O-acylating phenols of the formula (II). According to this process phenols of the formula (II) are reacted with N-carbamoyl-saccharin derivatives of the formula (IV)

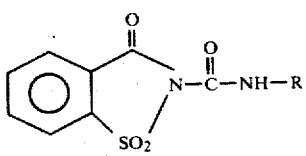

in the presence of bases.

As these bases inorganic bases we can use, preferably alkali metal hydroxides, carbonates, hydrocarbonates; alkali earth metal hydroxides, carbonates, hydrocarbonates; and tertiary amines, preferably triethyl amine. The base is expediently used at least in an amount stoichiometrically equivalent to the acylating agent of the formula (IV).

The reaction of the compounds of the formula (II) with the compounds of the formula (IV) is preferably carried out in an organic solvent, or in a mixture of an organic solvent and water. We can use as organic solvents hydrocarbons, lower ketones or esters (acetone, methylethyl ketone, ethyl acetate), ethers (dioxane, tetrahydrofurane), chlorinated solvents (chloroform, dichloroethane), lower acid amides (formamide, dimethyl formamide). It is preferred to use solvents in which at least two of the starting compounds (including the base) is soluble, and the compound of the formula (I) obtained is insoluble, or is dissolved but can be precipitated without accompanying impurities. When an inorganic base is used, the reaction product if desired, can be purified also by treating with water. The organic bases are more preferred, taking into account also the solubility of the salt-like adducts prepared therefrom in organic solvents, especially in solvent systems, in which the compound of the formula (I) obtained is insoluble while the organic base and its saccharin adduct are soluble.

The compounds of the formula (I) are reacted with the compounds of the formula (IV) at 0° C. to 100° C., preferably at room temperature, expediently under stirring. The compounds obtained are preferably isolated by crystallization or precipitation with a suitable solvent, while saccharin split off during the reaction remains in the solution as a salt formed with the base employed. From this salt saccharin can easily be isolated and can repeatedly be used for the preparation of an acylating agent of the formula (IV).

While according to the methods known in the art compounds of the formula (I) could be prepared only by an addition or a two-step substitution reaction, according to the invention these compounds are obtained in a one-step substitution reaction. Accordingly, the compounds of the formula (I) can be prepared in an aqueous medium.

A further advantage of the process according to the invention consists in the fact that no toxic, gaseous or liquid acylating agents are used. The N-carbamoyl-saccharin derivatives are crystalline solids, which are easy to handle and can unrestrictedly be stored. Since the acylation carried out by using these agents is far less exothermic than, for example, acylation performed with isocyanates, the undesired side-reactions can be avoided and compounds of the formula (I) can be prepared in a high purity, with excellent yield.

According to a further feature of the invention there is provided an acylating composition suitable for acylating phenolic hydroxyls, which contains 5 to 50% by weight of a compound of the formula (IV), wherein R is as hereinbefore defined, in admixture with 0.20 to 30% by weight but at least equivalent amount of a base and 10 to 80% by weight of a solvent.

The preferred acylating compositions contain as an acylating agent N-phenyl-carbamoyl-benzoic acid sulfinide, N-methyl-carbamoyl-benzoic acid sulfinide, N-butyl-carbamoyl-benzoic acid sulfinide, N-(methyl-phenyl)-carbamoyl-benzoic acid sulfinide, in admixture with triethyl amine as a base and acetone as a solvent.

Further details of our invention are illustrated by the following Examples. It is, however, by no means intended to limit our invention to the Examples.

EXAMPLE 1

4.3 g (0.025 moles) of methyl-(N-3-hydroxyphenyl)-carbamate are reacted with 7.3 g (0.025 moles) of N-phenylcarbamoylbenzoic acid sulfimide (m.p.: 184°–186° C.) in 15 ml of acetone, in the presence of 2.56 g (0.025 moles) of triethyl amine, at 40° C. for 15 minutes. To the reaction mixture 40 ml of water are added and it is cooled to 5° to 10° C. The mixture is allowed to stand for 30 minutes, filtered, washed and dried. 5.5 g of 3-methoxycarbonylaminophenyl-phenyl carbamate are obtained, melting at 150° to 152° C.

Benzoic acid imide can be precipitated from the mother liquor by hydrochloric acid.

EXAMPLE 2

3.35 g (0.025 moles) of 2,3-dihydro-2,2-dimethyl-benzofuran-7-ole are reacted with 6 g (0.025 moles) N-methylcarbamoyl-benzoic acid sulfimide in 15 ml of acetone, in the presence of 2.56 g (0.025 moles) of triethyl amine, at 50° C. for 15 minutes. The reaction mixture is then cooled to room temperature, diluted with 100 ml of water, the precipitate is filtered off, washed with water and dried. 3.1 g of 2,3-dihydro-2,2-dimethyl-benzofurane-7-yl methylcarbamate are obtained, melting at 150° to 152° C. Benzoic acid sulfimide can be recovered by precipitation from the mother liquor with an acid.

EXAMPLE 3

1.5 g of N-methylcarbamoyl-benzoic acid sulfimide are suspended in a mixture of 1 g of 2,3-dihydro-2,2-dimethylbenzofurane-7-ole in 5 ml of acetone and 5 ml of water, whereupon a solution of 0.6 g of triethyl amine in a mixture of 2 ml of acetone and 1 ml of water is added dropwise, at room temperature with stirring, in 20 minutes. 20 ml of water are then added dropwise in 30 minutes, and the mixture is stirred for another 1.5 hours. The precipitated crystals are filtered off, washed with water and dried. 0.745 g of 2,3-dihydro-2,2-dimethylbenzofurane-7-yl methylcarbamate are obtained, melting at 150° to 152° C.

EXAMPLE 4

4.3 g (0.025 moles) of methyl-(N-3-hydroxyphenyl)-carbamate are refluxed with 7.3 g (0.025 moles) of N-phenyl-carbamoyl-benzoic acid sulfimide (m.p.: 184° to 186° C.) in 15 ml of acetone, in the presence of 2 g (0.0145 moles) of potassium carbonate for 15 minutes. 40 ml of water are then added and the mixture is cooled to 5° to 10° C. After standing for 1 hour, the precipitated crystals are filtered off, washed and dried. 5.8 g of 3-methoxycarbonylamino-phenylcarbamate are obtained, melting at 150° to 152° C.

EXAMPLE 5

4.5 g (0.025 moles) of ethyl-(N-3-hydroxyphenyl)-carbamate are reacted with 7.3 g (0.025 moles) of N-phenyl-carbamoyl-benzoic acid sulfimide in 15 ml of acetone, in the presence of 2.56 g (0.025 moles) of triethyl amine at 40° C. for 15 minutes. Upon addition of 40 ml of water the reaction mixture is cooled to 5° C., allowed to stand for 30 minutes, filtered, washed and dried. 5.7 g of 3-ethoxycarbonyl-aminophenyl-phenyl-carbamate are obtained, melting at 117° to 119° C.

EXAMPLE 6

4.3 g (0.025 moles) of methyl-(N-3-hydroxyphenyl)-carbamate are reacted with 7.9 g (0.025 moles) of N-(3-methylphenyl)-carbamoyl-benzoic acid sulfimide in 15 ml of acetone, in the presence of 2.56 g (0.025 moles) of triethyl amine at 30° C. for 30 minutes. Upon addition of 50 ml of water the reaction mixture is cooled to 5° to 10° C., allowed to stand for 30 minutes, filtered, washed and dried. 5.3 g of 3-methoxycarbamoylphenyl-3'-methyl-phenyl-carbamate are obtained, melting at 140° to 142° C.

By precipitation with hydrochloric acid 3.5 g (76%) of benzoic acid sulfimide are recovered. This method can equally be employed in any of the preceding examples.

EXAMPLE 7

5 g. N-methyl-carbamoyl-benzoic acid sulfimide are suspended in a mixture of 2.67 g. of 2-chlorophenol and 50 g. acetone. The mixture is then cooled to 5° C. and while stirring a solution of 2.9 ml triethylamine in 30 ml acetone is added dropwise. The temperature of the mixture during addition (two hours) was not allowed to increase above 6° C. After standing for 12 hours and stirring at a temperature of 5° C. 240 ml of distilled water was added in portions to the mixture then extracted with 3×30 ml ether. The ethereal extracts were dried with sodium sulfate, then the solvent was evaporated in vacuum at a temperature not above 30° C.

3.13 g. 2-Chlorphenyl N-methyl-carbamate are obtained, after recrystallization from N-pentane, melting at 90°–91° C.

EXAMPLE 8

5 g. N-methyl-carbamoyl-benzoic acid sulfimide are suspended in a mixture of 2.6 g. methoxyphenyl and 50 ml acetone and while stirring at room temperature, a solution of 2.9 ml triethylamine in 30 ml acetone was added dropwise, in an hour. The mixture is stirred for further 2 hours at room temperature, then 240 ml distilled water is slowly added to the mixture and extracted with 3×30 ml ether. The ethereal extract is dried with sodium sulfate, then the solvent evaporated in vacuum at a temperature not above 30° C. 2.43 g. 2-methoxy-phenyl N-methyl-carbamate are obtained, recrystallized from N-pentane, melting at 90°–92° C.

EXAMPLE 9

2.4 g. N-methyl-carbamoyl-benzoic acid sulfimide are suspended in a mixture of 1.63 g. 2-methoxy-4-cianomethylene-phenol in 15 ml. acetone, and while stirring at room temperature a solution of 1.4 ml triethylamine in 5 ml acetone is added, in an hour. After standing another 2 hours at room temperature 65 ml distilled water is added to the mixture. After standing for 16 hours at 5° C. the precipitated crystals are filtered off, washed with water and dried. 0.72 g. product is obtained, melting at 138°–139° C., Analysis: Calculated: C-O/O; 59.99, H-O/O; 5.45, N-O/O; 12.72; Found: C-O/O; 60.05, J-O/O; 5.52, N-O/O; 12.65.

The remaining liquid after the crystallization is washed with 3×10 ml ether, the ethereal extracts dried with sodium sulfate, then in vacuum at a temperature not above 30° C. the solvent was evaporated, an additional 0.95 g. methoxy-4-cianomethylene-phenyl N-methyl-carbamate was obtained.

EXAMPLE 10

5 g. N-butyl-carbamic acid benzoic acid sulfimide are suspended in the mixture of 1.67 g. phenol and 50 ml water, then while stirring (5 hours) a solution of 0.71 g. sodium hydroxyd in 50 ml water is added. After stirring another 3 hours the mixture is extracted with 2×30 ml ether. The ethereal extracts dried with sodium sulfate, then the solvent evaporated in vacuum at a temperature not above 30° C. 2.15 g. phenyl N-butyl-carbamate are obtained, which can be distilled at 146°–148° C. at 2 mmHg.

EXAMPLE 11

5 g. N-tertiary butyl-carbamoyl-benzoic acid sulfimide and 1.9 g. 4-methyl-phenol in 50 ml chloroform is heated to boiling point, then while stirring a mixture of 2.5 ml triethylamine and 30 chloroform is added, in an hour. After boiling an hour the solvent is evaporated in vacuum, the oily residue mixed with ether. The precipitated benzoic acid sulfimide triethyl amine salt is filtered then, the ethereal solution evaporated in vacuum at a temperature not above 30° C.

2.4 g. 4-methyl-phenyl N-tertiary butyl carbamate is obtained, melting at 130°–132° C. after crystallized from petrolether.

We claim:

1. An acylating composition for the acylation of phenolic hydroxyl groups, which comprises 5 to 50% by weight of a saccharin derivative of the formula (IV)

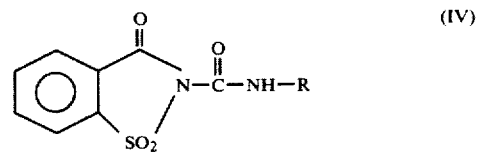

wherein
R is alkyl having 1 to 8 carbon atoms, aryl, cycloalkyl having 5 or 6 carbon atoms, aralkyl having 7 to 16 carbon atoms, which can be substituted by one or more alkyl groups having 1 to 4 carbon atoms,
in admixture with 0.2 to 3% by weight but at least an equivalent amount of a base and 10 to 80% by weight of a solvent.

2. A composition as claimed in claim 1, which comprises as the saccharin derivative N-phenylcarbamoyl-benzoic acid sulfinide, N-methylcarbamoyl-benzoic acid sulfinide, N-butyl-carbamoyl-benzoic acid sulfinide or N-(methylphenyl)-carbamoyl-benzoic acid sulfinide.

3. A composition as claimed in claim 1, which comprises triethyl amine as a base, and acetone as a solvent.

* * * * *